(12) United States Patent
Yang et al.

(10) Patent No.: US 7,550,507 B2
(45) Date of Patent: Jun. 23, 2009

(54) 2-(ALPHA-HYDROXYPENTYL) BENZOATE AND ITS PREPARATION AND USE

(75) Inventors: Jinghua Yang, Beijing (CN); Xiaoliang Wang, Beijing (CN); Zhibin Xu, Beijing (CN); Ying Peng, Beijing (CN)

(73) Assignee: Institute of Materia Medica, Chinese Academy of Medical Sciences, Beijing (CN)

( * ) Notice: Subject to any disclaimer, the term of this patent is extended or adjusted under 35 U.S.C. 154(b) by 284 days.

(21) Appl. No.: 10/512,792

(22) PCT Filed: May 9, 2002

(86) PCT No.: PCT/CN02/00320

§ 371 (c)(1),
(2), (4) Date: May 27, 2005

(87) PCT Pub. No.: WO03/095412

PCT Pub. Date: Nov. 20, 2003

(65) Prior Publication Data

US 2005/0288263 A1    Dec. 29, 2005

(51) Int. Cl.
*A61K 31/19* (2006.01)
*C07C 65/00* (2006.01)

(52) U.S. Cl. ...................................... 514/568; 562/473
(58) Field of Classification Search ................. 514/159, 514/568; 560/98; 562/473
See application file for complete search history.

(56) References Cited

FOREIGN PATENT DOCUMENTS

| CN | 1 283 621 | 2/2001 |
|---|---|---|
| CN | 1 382 682 | 12/2002 |

OTHER PUBLICATIONS

Berge et al , Journal of Pharmaceutical Sciences, Jan. 1977, p. 1-18.*
English Translation of Claims of CN 1 283 621 Dated Feb. 14, 2001.
English Translation of Claims and Abstract of CN 1 382 682 dated Dec. 4, 2002.

* cited by examiner

*Primary Examiner*—Taylor Victor Oh
(74) *Attorney, Agent, or Firm*—Ladas and Parry LLP

(57) ABSTRACT

The invention relates to new synthetic 2-(α-hydroxypentyl) benzoates, their preparation and pharmaceutical compositions containing such salts as active ingredients. The invention also relates to the use of the compounds for preventing and treating cardioischemia, cerebroischemia and cardiac or cerebral arterial occlusion (obstruction), etc.

5 Claims, No Drawings

2-(ALPHA-HYDROXYPENTYL) BENZOATE AND ITS PREPARATION AND USE

TECHNICAL FIELD

This invention relates to new chemically synthetic 2-(α-hydroxypentyl)benzoates, their preparations and pharmaceutical compositions containing the salts as active ingredients. This invention also relates to the uses of the compounds in the prevention and treatment of the diseases such as cardioischemia, cerebroischemia, heart and brain arterial occlusions, etc.

BACKGROUND OF THE INVENTION

Acute ischemic cerebral apoplexy is a common disease with high incidence (12-18 cases per ten thousands) and high death rate (6-12 cases per ten thousands) which seriously endangers human's health, which often leaves sequela in the survivals and imposes a heavy burden on the patients' family and society. Therefore, it is very valuable of developing drug for the prevention and treatment of the disease. Many researchers have been studying the mechanism of the disease (acute ischemic cerebral apoplexy) since the 1980's, and have proposed theories such as energy metabolism, excitatory poison, oxidative injury, calcium overload and many other theories for the purpose of developing high effective and low toxic drugs. However, an ideal therapeutic drug is still under developing. Drugs such as calcium antagonists, excitatory receptor antagonists, free radical scavengers are being clinically used, but the effects are uncertain. Thrombolytic drugs such as t-PA are being used to treat acute ischemic cerebral apoplexy (within 6 hrs from incidence), and is effective, but the hazard of hemorrhage has not been solved. Thus it is still a focus of developing new drugs to treat ischemic cerebral apoplexy.

Coronary heart disease is also a severe disease which harms human's health. Due to the coronary atherosclerosis and the formation of thrombus, ischemic cardiac muscle trauma is induced. For this reason, it has been being a leading work of developing new drugs to prevent and treat coronary atherosclerosis, prevent thrombus formation and dilatate coronary artery.

SUMMARY OF THE INVENTION

The object of the present invention is to provide new 2-(α-hydroxypentyl)benzoates which can significantly inhibit platelet aggregation and ameliorate cerebral microcirculation and effective to cardioischemia, cerebroischemia, heart and brain arterial occlusions.

Another object of the present invention is to provide a synthetic method of 2-(α-hydroxypentyl)benzoates.

Yet another object of the present invention is to provide a pharmaceutical composition which can prevent and treat cardioischemia, cerebroischemia, heart and brain arterial occlusions.

The fourth object of the present invention is to provide use of the above compounds and pharmaceutical compositions in the prevention and treatment of cardioischemia, cerbroischemia, heart and brain arterial occlusions, and amelioration of cerebral microcirculation.

The present invention provides a compound of the following general formula (I):

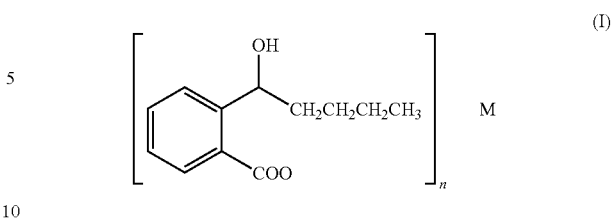

wherein n=1,2; M is a monovalent metal ion, such as $K^+$, $Na^+$, $Li^+$; a divalent metal ion, such as $Ca^{2+}$, $Mg^{2+}$, $Zn^{2+}$; or an organic basic group, such as anilino, benzyl amino, morpholinyl or diethylamino.

The preparation method of present invention is as following:

1. Preparation of 2-(α-hydroxypentyl)benzoates of general formula (I) wherein M is a monovalent metal ion:

Solving an equivalent racemic 3-n-butyl-isobenzofuran-1-(3H)-one in a hydrolysis and ring-opening reaction solvent medium, adding an equivalent or slightly excess amount of monovalent base. After that hydrolysis and ring-opening reaction is conducted under the temperature of 10-100° C., for 0.5-6 hours, to afford the 2-(α-hydroxypentyl)benzoates of general formula (I) wherein M is a monovalent metal ion.

The solvent for the hydrolysis and ring-opening reaction may be any one of methanol, ethanol, acetone, isopropanol, water or mixture of $H_2O$-alcohol (or ketone).

The crystallization solvent may be any one of methanol, ethanol, propanol, isopropanol, acetone, acetyl acetate, chloroform, ether, dichloromethane, benzene, toluene, petroleum ether, or a mixture of two or three above solvents with different proportions; monovalent base may be an inorganic base, such as a chemically pure inorganic base, for example sodium hydroxide, potassium hydroxide, or lithium hydroxide, etc; or a chemically pure organic base, such as sodium (or potassium) methoxide, sodium (or potassium) ethoxide, etc.

2. Preparation of 2-(α-hydroxypentyl)benzoates of general formula (I) wherein M is a divalent metal ion:

2-(α-Hydroxypentyl)benzoate of general formula (I) wherein M is a monovalent metal ion (e.g., sodium or potassium) is solved in a solvent, then an equivalent or slightly excess amount of chemically pure divalent metal salt is added and an ion-exchange reaction is conducted under the temperature of 10-100° C. for 0.5-10 hours to afford the 2-(α-hydroxypentyl)benzoates of general formula (I) wherein M is a divalent metal ion.

The reaction solvent medium is methanol, ethanol, acetone, isopropanol, water or a mixture of water-alcohol (or ketone); divalent metal salt may be magnesium chloride, calcium chloride, or zinc chloride; the crystallization solvent may be methanol, ethanol, isopropanol, acetyl acetate, chloroform, ether, dichloromethane, or a mixture of two or three above solvents with different proportions.

3. Preparation of the 2-(α-hydroxypentyl)benzoates of general formula (I) wherein M is an organic base:

(1) 2-(α-hydroxypentyl)benzoate of general formula (I) wherein M is a monovalent metal ion (e.g., sodium or potassium) is solved in a solvent, then a inorganic acid is added to the solution to adjust pH value to 6.0-2.0 at the temperature of −20-20° C., preferably −20-0° C., to acidify the 2-(α-hydroxypentyl)benzoate and 2-(α-hydroxypentyl)benzoic acid is obtained.

(2) After the reaction is completed, an organic extraction solvent is added to the solution and the free acid 2-(α-hydroxypentyl)benzoic acid is extracted with common extraction method at a temperature of −20-0° C. An organic solution containing 2-(α-hydroxypentyl)benzoic acid is obtained and the solution is kept for use under the temperature of −20-10° C., preferably −20~0° C.

(3) To the solution obtained in the above step, a solution which contains an equivalent or slightly excess amount of monovalent base to the 2-(α-hydroxypentyl)benzoic acid, for example an alcohol solution of potassium hydroxide, is added, at the temperature of −10~0° C., to afford the 2-(α-hydroxylpentyl)benzoate of present invention wherein M is a monovalent metal ion, such as potassium. After the reaction is sufficiently conducted, with a same purification method with that of preparation method 1, the compound of present invention, i.e., 2-(α-hydroxylpentyl)benzoate wherein M is a monovalent metal ion is prepared.

(4) To the solution obtained in step (2), a solution which contains an equivalent or slightly excess amount of divalent base or a divalent metal salt to the 2-(α-hydroxypentyl)benzoic acid, for instance an alcohol solution of calcium hydroxide, is added, under the temperature of −10~0° C., to afford the 2-(α-hydroxypentyl)benzoate of present invention wherein M is a divalent metal ion, such as calcium. After the reaction is sufficiently conducted, with a same purification method with that of preparation method 2, the compound of present invention, i.e., 2-(α-hydroxylpentyl)benzoate wherein M is divalent metal ion is prepared.

(5) To the solution obtained in step (2), a solution which contains an equivalent or slightly excess amount of organic base to the 2-(α-hydroxypentyl)benzoic acid, for instance chemically pure aniline, is added, under the temperature of −10~0° C., to afford the 2-(α-hydroxypentyl)benzoate of present invention wherein M is an organic base, such as aniline. After the reaction is sufficiently conducted, with a same purification method with that of preparation method 2, the compound of present invention, i.e., 2-(α-hydroxylpentyl)benzoate wherein M is divalent metal ion is prepared.

The acid used in the acidify reaction may be any one of concentrated or diluted hydrochloric acid or sulfuric acid; the temperature should be controlled within the range of −20~+20° C.; the organic solvent to extract 2-(α-hydroxypentyl)benzoic acid may be any one of ether, ethyl acetate, chloroform, dichloromethane, benzene, toluene, petroleum ether, n-hexane, or cyclohexane; the monovalent base is selected from potassium hydroxide, sodium hydroxide, lithium hydroxide, sodium (or potassium) methoxide, or sodium (or potassium) ethoxide; the divalent inorganic metal salt or divalent inorganic base is selected from $MgCl_2$, $MgCO_3$, $CaCl_2$, $CaCO_3$, $ZnCl_2$, $ZnCO_3$, $MgSO_4$, $Zn(OH)_2$, $Mg(OH)_2$ or $Ca(OH)_2$; the organic base is selected from aniline, benzyl amine, morpholine or diethylamine; the solvent to solve the 2-(α-hydroxylpentyl)benzoate wherein M is a monovalent metal salt may be any one of $H_2O$, MeOH—$H_2O$, EtOH—$H_2O$, acetone-$H_2O$, isopropanol-$H_2O$.

It has been found that the present compounds show good effects on prevention and therapeutics to cardioischemia and cerebroischemia, further, the present compounds also have pharmacological effects of anti-platelet aggregation, arterial occlusion of heart and brain therapeutic effect, and cerebral microcirculation amelioration effect, etc.

The present compounds have shown from animal tests excellent effects on protecting ischemic injury of heart, anti-platelet aggregation and alleviation of injury due to cerebral-arterial occlusion, moreover, no side effects such as exciting or hemorrhage have not been found.

The pharmaceutical composition of the prevent invention comprises an treatment effective amount of the compound of the present invention as active ingredient and a pharmaceutically acceptable carrier.

The compounds and pharmaceutical compositions of the prevent invention can be used for the preparation of drugs which can prevent and treat cardioischemia and cerebroischemia, arterial occlusion of heart and brain, amelioration of cardiac-cerebral microcirculations.

The above mentioned "pharmaceutically acceptable carrier" means the ordinary drug carriers such as diluents, excipients, fillers such as starch, saccharide; binders such as cellulose derivatives, alginates, gelatin, and polyvinylpyrrolidone; moisturizing agents such as glycerol; disintegrating agents such as agar, calcium carbonate and sodium bicarbonate; resorption accelerators such as quaternary ammonium compounds; surface active agents such as cetyl alcohol; adsorptive carriers such as kaolin and bentonite; lubricants such as talc, calcium or magnesium stearate, and polyethyleneglycols; further, other assistants such as flavors and sweeteners can also be added.

The compounds of this invention can be administered orally and intravenously to the patients in need of such treatment in a form of pharmaceutical formulation. When administrated orally, it can be administrated in the dosage form such as tablets, particles, or capsules. And it can be in the form of solutions or oily/aqueous suspensions for injection. Preferred dosage forms are tablet, capsule and injection.

The dosage forms of present pharmaceutical compositions can be prepared by common procedures in the art. For example, the compounds of this invention can be admixed with one or more carriers and formed into a desired dosage form.

The present pharmaceutical composition preferably contains active ingredients in a weight ratio of 3:2, most preferably 1:1.

The dose of present compound may vary based on administration route, age, weight, disease type and severeness of disease of the patient being treated. A typical daily dose may be from 50 mg to 600 mg per day, preferably 100~200 mg per day, which can be administered once or more times.

DETAILED DESCRIPTION OF THE INVENTION

The following examples are only illustrative and are not intended to limit the scope of the present invention.

EXAMPLE 1

Preparation of Racemic Potassium 2-(α-hydroxypentyl) benzoate (Herein After also Referred as Potassium dl-2-(α-hydroxypentyl) benzoate, or dl-PHPB)

Dissolving dl-3-n-Butyl-isobenzofuran-1-(3H)-one (8.5 g, 0.045 mol) in 20 ml methanol and a 10 ml methanol solution of KOH (2.6 g, 0.046 mol) was added. The reaction solution was stirred under reflux for one hour. After that, TLC analysis (petroleum ether-acetone=10:1) and $I_2$ vapor coloration showed that the starting material was disappeared. The reaction solution was concentrated under reduced pressure to afford a sticky yellow residue, which was allowed to crystallize in the refrigerator after addition of 20 ml of chloroform.

The crude product was recrystallized in MeOH—CHCl₃, and a white granular crystal (10.07 g, yield=91.50%) was obtained.

EXAMPLE 2

Preparation of Potassium dl-2-(α-hydroxypentyl)benzoate

Dissolving dl-3-n-Butyl-isobenzofuran-1-(3H)-one (0.63 g, 3.3 mmol) in 10 ml methanol and a 10 ml methanol solution of KOH (0.19 g, 3.4 mmol) was added. The reaction solution was stirred under reflux for one hour. After that, TLC analysis (petroleum ether-acetone=10:1) and I₂ vapor coloration showed that the starting material was disappeared. The reaction solution was concentrated under reduced pressure to afford a sticky yellow residue, which was allowed to crystallize in the refrigerator after addition of 5 ml of chloroform. The crude product was recrystallized in MeOH—CHCl₃, and a white granular crystal (0.6 g, yield=73.56%) was obtained.

EXAMPLE 3

Preparation of Potassium dl-2-(α-hydroxypentyl)benzoate

Dissolving sodium dl-2-(α-hydroxypentyl)benzoate (1.96 g, 8.5 mmol) in 10 ml of H₂O and the solution was cooled to about 0° C. in an ice-salt bath. The pH was adjusted to 2.0~3.0 with 1N HCl and the solution was extracted quickly with cold ether (3×20 ml). The ether extract was combined and dried with anhydrous Na₂SO₄ at a low temperature for 3 hours and then filtered quickly under the low temperature. To the filtrate a 20 ml methanol solution of anhydrous K₂CO₃ (0.58 g, 4.2 mmol) was added and the mixture was stirred fastly to ambient temperature. A white solid appeared in the ether solution and the solution was kept for over 24 hours, then the white solid was filtered and dried (1.4 g, yield=66.67%).

EXAMPLE 4

Preparation of Potassium dl-2-(α-hydroxypentyl)benzoate

Dissolving sodium dl-2-(α-hydroxypentyl)benzoate (1.78 g, 7.7 mmol) in about 10 ml of H₂O and the solution was cooled to about 0° C. in an ice-salt bath. The pH was adjusted to 2.0~3.0 with 1N HCl and the solution was extracted quickly with cold ether (3×20 ml). The ether layer was combined and dried with anhydrous Na₂SO₄ at a low temperature for 2 hours and then filtered quickly under the low temperature. To the filtrate a 10 ml methanol solution of KOH (0.43 g, 7.7 mmol) was dropped in and the mixture was kept in the ice-salt bath to ambient temperature. After concentration under reduced pressure, the residue was recrystallized with MeOH-ether. A white solid was obtained (1.3 g, yield=68.42%).

The potassium dl-2-(α-hydroxypentyl)benzoate as prepared in the above Examples 1 till 4 procedures is a white granular crystal.

mp. 151-152° C.

IR(KBr) 3198 cm⁻¹($v_{OH}$), 2933 cm⁻¹($v_{CH_3}$), 1577, 1561 ($v_{COO}$)

¹H-NMR (300 MHz, DMSO) δ(ppm) 7.65 (dd, J=6.3 Hz, 2.7 Hz, 1H), 7.17-7.05 (m, 3H), 4.32 (t, 1H), 3.40 (s, 1H), 1.80-1.55 (m, 2H), 1.38-1.04 (m, 4H), 0.81 (t, 3H)

Elemental Analysis C₁₂H₁₅O₃K(FW246.35)

| | C(%) | H(%) | K(%) |
|---|---|---|---|
| Calculated | 58.51 | 6.14 | 15.87 |
| Found | 58.24 | 6.01 | 15.84 |

MS£"EI£ © m/z

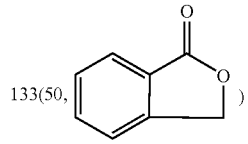

133(50, )

EXAMPLE 5

Preparation of Sodium dl-2-(α-hydroxypentyl)benzoate

Dissolving dl-3-n-Butyl-isobenzofuran-1-(3H)-one (4.6 g, 0.024 mol) in 20 ml methanol and a 10 ml aqueous solution of NaOH (0.86 g, 0.022 mol) was added. The reaction solution was stirred under reflux for 2 hours. After that, TLC analysis (petroleum ether-acetone=10:1) and I₂ vapor coloration showed that the starting material was disappeared. The reaction solution was concentrated under reduced pressure to afford a sticky yellow residue, which did not crystallize in the solvents such as chloroform, acetone, ether or methanol, etc. A small amount of residue was solidified with ether-ethyl acetate (10:1) to afford a white solid, which was very hydroscopic and became sticky over filtration. The yellow residue was washed with ether for several times and dehydrated with anhydrous benzene, dried under reduced pressure to afford a white foamed solid (3.67 g, yield=65.91%).

EXAMPLE 6

Preparation of Sodium dl-2-(α-hydroxypentyl)benzoate

Dissolving dl-3-n-Butyl-isobenzofuran-1-(3H)-one (7.6 g, 0.04 mol) in 20 ml methanol and a fresh methanol solution (20 ml) of sodium methoxide (0.92 g, 0.04 mol of Na) was added. The reaction solution was stirred under reflux for 2 hours. After that, TLC analysis (petroleum ether-acetone=10: 1) and I₂ vapor coloration showed that the starting material was disappeared. The reaction solution was concentrated under reduced pressure to afford a sticky yellow residue, which did not crystallize in the solvents such as chloroform, acetone, ether or methanol, etc. The yellow residue was washed with ether for several times and dehydrated with anhydrous benzene, dried under reduced pressure to afford a white foamed solid (6.4 g, yield=69.56%).

EXAMPLE 7

Preparation of Sodium dl-2-(α-hydroxypentyl)benzoate

Dissolving dl-PHPB (1.0 g, 0.004 mol) in 10 ml of H₂O and the solution was cooled to about 0° C. in an ice-salt bath. The pH was adjusted to 2.0~3.0 with 1N HCl and the solution was extracted quickly with cold ether (3×20 ml). The ether extract was combined and dried with anhydrous Na₂SO₄ at a low temperature for 2 hours and then filtered quickly under the low temperature. To the filtrate a 20 ml methanol solution of anhydrous $Na_2CO_3$ (0.58 g, 4.2 mmol) was added and the solution became turbid and return clear after 3 hours of standing with ice-salt bath. The reaction solution was concentrated under reduced pressure to afford a sticky yellow residue, which was washed with ether for several times and dehydrated with anhydrous benzene, dried under reduced pressure to afford a white foamed solid (0.4 g, yield=42.78%).

EXAMPLE 8

Preparation of dl-Sodium-2-(α-hydroxypentyl)benzoate

Dissolving dl-PHPB (2.4 g, 0.01 mol) in 20 ml of $H_2O$ and the solution was cooled to about 0° C. in an ice-salt bath. The pH was adjusted to 2.0~3.0 with 1N HCl and the solution was extracted quickly with cold ether (3×20 ml). The ether extract was combined then a 20 ml methanol solution of NaOH (0.39 g, 0.01 mol), the resulted solution was kept over night in the ice-salt bath. After concentration under reduced pressure, a sticky yellow residue was afforded, which was processed as above, and a white foamed solid (1.2 g, yield=53.48%) was afforded.

The sodium dl-2-(α-hydroxypentyl)benzoate as prepared in the above Examples 5 till 8 procedures is a foamed white solid.

IR (film) 3398 $cm^{-1}(v_{OH})$, 2969 $cm^{-1}(v_{CH3})$, 1558, 1394 $cm^{-1}(v_{COO})$ $^1$H-NMR (300 MHz,DMSO) δ(ppm) 7.70 (dd, J=6.9 Hz, 1.8 Hz, 1H), 7.17-7.07 (m, 3H), 4.39 (t, 1H), 1.65-1.48 (m, 2H), 1.39-1.10(m, 4H), 0.83(t, 3H)

EXAMPLE 9

Preparation of Lithium dl-2-(α-hydroxypentyl)benzoate

Dissolving dl-3-n-Butyl-isobenzofuran-1-(3H)-one (1.2 g, 0.006 mol) in 15 ml methanol and $LiOH.H_2O$ (0.26 g, 0.006 mol) was added. The reaction solution was stirred under reflux for 2 hours. After that, TLC analysis (petroleum ether-acetone=10:1) and $I_2$ vapor coloration showed that the starting material was disappeared. The reaction solution was concentrated under reduced pressure to afford a white crystal (1.1 g, yield=81.38%).

mp. 134-136° C.

IR(KBr) 3323 $cm^{-1}(v_{OH})$, 2931 $cm^{-1}(v_{CH3})$, 1604, 1414 $cm^{-1}(v_{COO})$ $^1$H-NMR (300 MHz,DMSO) δ(ppm) 7.66(dd, 1H), 7.17-7.16(m, 3H), 4.32(t, 1H), 1.78-1.54(m, 2H), 1.27-1.02(m, 4H), 0.84(t, 3H)

Elemental Analysis $C_{12}H_{15}O_3Li$(FW214.19)

|  | C(%) | H(%) | Li(%) |
|---|---|---|---|
| Calculated | 67.29 | 7.06 | 3.24 |
| Found | 67.34 | 6.87 | 3.26 |

EXAMPLE 10

Preparation of Calcium dl-2-(α-hydroxypentyl)benzoate

Dissolving dl-3-n-Butyl-isobenzofuran-1-(3H)-one (1.4 g, 7.1 mmol) in 15 ml methanol and a 20 ml aqueous solution of NaOH (0.28 g, 7.0 mmol) was added. The reaction solution was stirred under reflux for 2 hours. After that, TLC analysis (petroleum ether-acetone=10:1) and $I_2$ vapor coloration showed that the starting material was disappeared. Calcium chloride (0.4 g, 4.5 mmol) was solved in 40 ml of $H_2O$, and the solution was dropped into the above reaction solution. The reaction was carried out in a 60° C. water bath for 2 hours, and the pH was adjusted to about 7 with 1N HCl and then reaction solution was filtered. The filtrate was concentrated to 10 ml under reduced pressure and a white solid appeared. The solution with the white solid appeared was kept for 30 minutes and then filtered. The filter cake was washed several times with water and $H_2O$-MeOH (1:1), respectively, until no chloride ion can be detected. Heating the filter cake to dry to afford a white solid (1.08 g, yield=33.23%).

EXAMPLE 11

Preparation of Calcium dl-2-(α-hydroxypentyl)benzoate

Dissolving dl-3-n-Butyl-isobenzofuran-1-(3H)-one (1.1 g, 5.8 mmol) in 20 ml anhydrous ethanol and a 10 ml aqueous solution of NaOH (0.39 g, 9.8 mmol) was added. The reaction solution was stirred under reflux for 2 hours. After that, TLC analysis (petroleum ether-acetone=10:1) and $I_2$ vapor coloration showed that the starting material was disappeared. The reaction solution was cooled to about 0° C. in an ice-salt bath, and acidified to pH 5.0~6.0 with 1N HCl, additional 20 ml ethanol was added to solve the precipitated white solid. Calcium carbonate powder (0.33 g, 3.3 mmol) was added and the reaction solution was stirred vigorously under low temperature and kept over night. A white solid appeared from the reaction solution and the reaction solution was filtered. The filter cake was washed several times with $H_2O$-MeOH. Heating the filter cake to dry to afford a white solid (0.65 g, yield=24.73%).

EXAMPLE 12

Preparation of Calcium dl-2-(α-hydroxypentyl)benzoate

Calcium chloride (0.12 g, 0.002 mmol) was dissolved in 20 ml $H_2O$, and heated to about 60° C. To the solution a 10 ml aqueous solution of dl-PHPB (0.5 g, 0.001 mol) was added. After a while, a white solid appeared and the reaction was continued for another 3 hours. After that, the reaction solution was filtered and the filter cake was washed with hot water and dried under heating to obtain a white solid (0.21 g) and the filtrate was concentrated under reduced pressure and washed with hot water and heated to dry, additional 0.15 g of white solid was obtained. The combined total white solid was 0.36 g (yield=78.02%).

Calcium dl-2-(α-hydroxypentyl)benzoate as prepared in the above Examples 9 till 12 procedures is a white solid, which decomposes above a temperature of 252° C.

IR (KBr) 3323 $cm^{-1}(v_{OH})$, 2931 $cm^{-1}(v_{CH3})$, 1604, 1401 $cm^{-1}(v_{COO})$ $^1$H-NMR (300 MHz,DMSO) δ(ppm) 7.56 (d, 1H), 7.24-7.05 (m, 3H), 4.55 (t, 1H), 1.71-1.52 (m, 2H), 1.26-1.04 (m, 4H), 0.80(t, 3H)

Elemental Analysis $C_{24}H_{30}O_6Ca$ (FW454.57)

|  | C(%) | H(%) | Ca(%) |
|---|---|---|---|
| Calculated | 63.41 | 6.65 | 8.82 |
| Found | 63.20 | 6.61 | 9.02 |

EXAMPLE 13

Preparation of dl-2-(α-hydroxypentyl)Benzoic Acid Benzyl Amine Salt

Dissolving dl-3-n-Butyl-isobenzofuran-1-(3H)-one (1.4 g, 7.1 mmol) in 15 ml methanol and a 20 ml aqueous solution of NaOH (0.28 g, 7.0 mmol) was added. The reaction solution was stirred continuously under reflux for 2 hours. After that, TLC analysis (petroleum ether-acetone=10:1) and $I_2$ vapor coloration showed that the starting material was disappeared. The reaction solution was cooled to about 0° C. in an ice-salt bath and acidified with 1N HCl to pH 3.0-4.0, and the solution was extracted quickly with cold ether (3×20 ml). The ether extract was combined and dried with anhydrous $Na_2SO_4$ at a low temperature and then filtered. Benzyl amine (0.9 ml, 8.24 mmol) was added to the reaction solution and the reaction solution was kept over night in the ice-salt bath. After concentration under reduced pressure, a yellow sticky residue was obtained and a white solid (1.07 g) seperated under the addition of petroleum ether—ether, which was recrystallized in ethyl acetate to afford a white crystal (0.61 g, yield=26.28%).

mp. 86-88° C.

IR (KBr) 3396 cm$^{-1}$($v_{NH}$), 2927 cm$^{-1}$(br, $v_{OH}$), 1637 cm$^{-1}$ ($v_{C=C}$) 1515 cm$^{-1}$($v_{COO}$)

$^1$HNMR (300 MHz, DMSO) δ (ppm) 7.65-7.13(m, 9H,), 4.67(t, 1H, CH), 3.95(d, 2H,CH$_2$), 1.58-1.66(m, 2H, CH$_2$), 1.14-1.34(m, 4H, CH$_2$CH$_2$), 0.82(t, 3H, CH$_3$)

Elemental Analysis $C_{19}H_{25}NO_3$(FW315.41)

|  | C(%) | H(%) | N(%) |
|---|---|---|---|
| Calculated | 72.35 | 7.99 | 4.44 |
| Found | 72.32 | 7.98 | 4.76 |

MS£"EI£ © m/z

133(50, 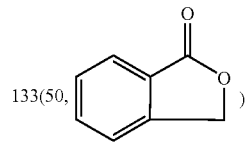)

EXAMPLE 14

Preparation of Pharmaceutical Compositions

| Tablets | |
|---|---|
| Ingredient | Amount (mg/tablet) |
| Active ingredient | 50~200 |
| Medicinal starch | 20~50 |
| Microcrystalline cellulose | 15~35 |

-continued

| Tablets | |
|---|---|
| Ingredient | Amount (mg/tablet) |
| Magnesium stearate | 0.5 |
| Talc | 0.5~1 |
| Sodium carboxymethyl cellulose | 2~5 |

The active ingredient, starch, microcrystalline cellulose and sodium carboxymethyl cellulose were crushed and mixed. The mixture was moisturized homogenously and powdered, which were then sieved and dried and then sieved again. Magnesium stearate and talc were mixed with the above mixture and the mixture was compressed to tablets, and the tablets were coated with a film coating (which may be hydroxypropylmethyl cellulose and the like). Each tablet contains 50~200 mg of active ingredient.

EXAMPLE 15

Preparation of Pharmaceutical Compositions

| Capsules | |
|---|---|
| Ingredient | Amount (mg/capsule) |
| Active ingredient | 50~200 |
| Medicinal starch or mannitose | 20~50 |
| Methyl cellulose | 3~4 |
| Cross-linked PVP | 0.5~1 |

The active ingredient and excipients were mixed and sieved. The so-obtained mixture was filled into stomach-soluble hard capsules with determine amounts. Each capsule contains 50~200 mg of active ingredient.

EXAMPLE 16

Preparation of Pharmaceutical Compositions

| Intravenous solution | |
|---|---|
| Ingredient | Amount |
| Active ingredient | 50~100 mg/bottle |
| Sodium hydroxide | Appropriate |
| Water for injection or saline | 5~50 ml |

The active ingredient was dissolved in an appropriate amount of water for injection or isotonic saline and then filtered. Adjusting pH to 10.5 (which may vary from 9.0 to 10.5) with appropriate amount of NaOH. The intravenous solution was filled into bottles under sterilizing condition.

EXAMPLE 17

Preparation of Pharmaceutical Compositions

| Lyophilized intravenous injection | |
|---|---|
| Ingredient | Amount |
| Active ingredient | 50~100 mg/bottle |
| Sodium hydroxide | Appropriate |

The active ingredient was dissolved in an appropriate amount of water for injection and the pH was adjusted to 9.0~10.0 with NaOH. The solution was filtered and freeze-dried to afford a cake or powder. The lyophilized injection can be injected and transfused intravenously after it is solved in the 0.9% NaCl solution for injection or 5% glucose injection.

TEST EXAMPLE 1

Effect of the Present Compounds on the Infarction Area after Local Cerebral Ischemia in Rats (1) Materials and Methods Animal: male Wistar rats (250-280 g), from the Animal Center of the Chinese Academy of Medical Sciences.

Drugs:

dl-PHPB was dissolved in double distilled water.

2,3,5-triphenyltetrazolium chloride (TTC) was purchased from Beijing Chemical Plant.

Methods: Middle cerebral artery occlusion(MCAO): the rats were anesthetized by trichloroacetaldehyde monohydrate (350 mg/kg, ip). The left CCA was exposed through a middle neck incision and was carefully dissected free from surrounding nerves. The ICA and ECA were isolated. Then a 4 cm long 0.26 mm diameter nylon suture was inserted through proximal ECA into ICA for a length of 2.0 mm from the bifurcation. The wounds were sutured and the rats were released. The room temperature was kept 24-25° C. during the test.

Groups:

Animals were divided into two groups, 1) administration group: dl-PHPB (200 mg/kg) and HCl (pH 1.6) 0.5 ml (to mimic the acidic condition of the human stomach) were administrated per os (p.o) 30 minutes prior to ischemia; 2) Control group: double-distilled water and HCl (pH 1.6) 0.5 ml were administrated per os (p.o) 30 minutes prior to ischemia.

Infarction Measurement:

The anaesthetized animals were decapitated 24 hours after MCAO. Each brain were rapidly removed and kept in ice-cold saline (0-4° C.). After 10 minutes, the coronal section was sliced into five pieces after the removal of bulbus olfactus, cerebellum, and low brain stem. Upon cutting, the first cut was at the center point of the connection line of the polus anterior of cerebrum and the optic chiasm, the second cut was at the site of optic chiasm, the third was at the site of infundibulum stalk, and the fourth was between the infundibulum stalk and the caudal pole of posterior lobe. The sliced brain was kept in a 5 ml solution of TTC (4%) and $K_2HPO_4$ (1M), shaded and incubated at 37° C. for 30 minutes. During the incubation, slices were turned over every 7 -8 minutes. After staining, the normal cerebral tissue showed rosy color, but the infarcted tissue showed white color. The infarcted tissue was separated from the normal tissue and weighed. The infarction area is calculated from the weight percentage of the infarct tissue to the total cerebral tissue.

(2) Result

Effect of dl-PHBP to the cerebral infarct areas in the rats of permanent MCAO.

Table 1 showes the infarct area, the area of the dl-PHBP treated group is 19.83±3.53%, and that of the control is 26.99±3.51%. The infarction is significantly reduced (P<0.01) in the treated group compared to the control.

TABLE 1

| | Control group (%) | Treated group(%) |
|---|---|---|
| | 30.50 | 26.01 |
| | 27.08 | 20.24 |
| | 27.92 | 18.24 |
| | 30.64 | 22.74 |
| | 24.87 | 16.84 |
| | 27.44 | 15.93 |
| | 20.46 | 18.79 |
| X ± SD | 26.99 ± 3.51 | 19.83 ± 3.53** |

**P < 0.01 vs control group (3) Conclusion

Potassium 2-(α-hydroxypentyl)-benzoate, dl-PHPB) significantly reduced the cerebral tissue injury induced by MCAO and decreased the infarction areas.

TEST EXAMPLE 2

The Effect of the Present Compounds on Platelet Aggregation (1) Materials and Methods Animal: male Wistar rats (260-280 g), from the Animal Center of the Chinese Academy of Medical Sciences.

Drugs:

Potassium 2-(1-hydroxypentyl)-benzoate, dl-PHPB),

ADP, obtained from Shanghai Institute of Biochemistry, Acedemia Sinica.

Equipment: Platelet Aggregometer (type: PAT-4A MEGURO-KU, TOKYO, JAPAN.

Groups: Animals were divided into four groups:

1) Control group: double-distilled water (400 mg/kg) was adimistrated per os (p.o) 30 minutes prior blood sampling;

2) Dl-PHPB (400 mg/kg) was administrated per os (p.o) 30 minutes prior to the blood sampling;

3) Dl-PHPB (400 mg/kg) was administrated per os (p.o) 60 minutes prior to the blood sampling;

4) Dl-PHPB (200 mg/kg) was administrated per os (p.o) 30 minutes prior to the blood sampling;

Method:

After oral administration of dl-PHPB, blood was drawn from the carotid of rats at the time points of 30 and 60 minutes, respectively. Platelet rich plasma (PRP) and platelet poor plasma (PPP) were prepared upon common procedure. According to the method described by of Born, PRP (200 µl) was put on the Platelet Aggregometer and pre-incubated at 37° C. for 5 minutes and then ADP with the final concentration of 5 µmol/L was added to induce platelet aggregation. The maximum aggregation was measured 5 minutes after the addition of ADP.

(2) Results

Table 2 shows the inhibitory effect on platelet aggregation induced by ADP.

TABLE 2

| Groups | N | Rate of platelet aggregation (%) | Rate of inhibition (%) |
|---|---|---|---|
| Control | 7 | 0.5556 ± 0.0287 | — |
| dl-PHPB (400 mg/kg 30 min) | 7 | 0.4483 ± 0.0610** | 19.31 |
| dl-PHPB (400 mg/kg 60 min) | 9 | 0.4989 ± 0.0562* | 10.21 |
| dl-PHPB (200 mg/kg 30 min) | 8 | 0.5021 ± 0.0622 | 6.62 |

**P < 0.01,
*P < 0.05 vs Control group (3) Conclusion

Potassium 2-(1-hydroxypentyl)-benzoate, dl-PHPB) significantly inhibits platelet aggregation compared to the control group.

TEST EXAMPLE 3

The Protective Effects of dl-PHPB on Cardiac Arrythmia Induced by Ischemia-Reperfusion in Isolated Hearts on Rats (1) Materials and Methods Animals: male Wistar rats, 250-300 g, from the Animal Center of the Chinese Academy of Medical Sciences, randomly grouped.

Drugs:

dl-PHPB,

NaCl, from the Beijing Chemical Reagent Factory No. 2,

KCl and $MgSO_4$, Beijing Shuanghuan Chemical Reagents Factory, $KH_2PO_4$, Beijing Yili Fine Chemicals Co., Ltd.

$NaHCO_3$, Beijing Chemical Reagents Company

Glucose, Beijing Guohua Chemical Reagents Factory $CaCl_2$, Sigma.

Apparatus:

Langendoff perfusion system;

XD-7100 ECG, Shanghai Medical Electronic Devices Factory

Methods:

(1) remove the rat heart quickly after decapitation and put it into K—H solution at 4° C., fix the aorta to the perfusion system;

(2) perfuse the heart with K—H solution, 6-8 ml/min, 37±0.5° C., under the pressure of about 60 $mmH_2O$;

(3) connect the two copper electrodes to the cardiac apex and the bottom of the right atria and record the cardiogram;

(4) perporate under the left anterior descending branch of the coronary artery with 3/0 line;

(5) perfuse the heart for 10 minutes and record the normal cardiogram;

(6) ligate the left anterior descending branch of the coronary artery to make myocardial ischemia for 15 minutes;

(7) nip the line and resume the perfusion, record the change of cardiogram for 30 minutes (mainly on VF and Spasmic VT);

(8) dissolve the dl-PHPB at pH 1.5 to a desired concentration, add it into K—H solution to do the experiments.

(2) Results

Table 3 shows the protective effects of dl-PHPB on cardic arrythmia induced by ischemia-reperfusion in isolated hearts on rats

TABLE 3

| Group | N | Duration of Arrhythmia (min) | VT Incidence (%) | VT Duration (min) | Spasmic VT Incidence (%) | VF Incidence (%) | VE Incidence (%) |
|---|---|---|---|---|---|---|---|
| Control | 12 | 22.5 ± 9.5 | 100 | 8.2 ± 7.9 | 66.7 | 33.3 | 83.3 |
| dl-PHPB ($10^{-5}$ mol/L) | 6 | 23.3 ± 5.8 | 100 | 5.0 ± 6.5 | 50 | 33.3 | 66.7 |
| dl-PHPB ($10^{-4}$ mol/L) | 7 | 1.7 ± 0.6*** | 100 | 1.1 ± 0.6** | 0* | 0 | 42.9 |

VT: ventricular tachycardia
VF: ventricular fibrillation
VE: ventricular ectopic beats
*P < 0.05,
**P < 0.01,
***P < 0.001 compared with the control group (3) Conclusion Dl-PHPB can significantly shorten the duration of arrhythmia and VT induced by ishchemia-reperfusion in isolated hearts on rats, decreases the accidence of spasmic ventricular tachycardia, and shows significant protections on the ischemic injuries of hearts at the concentration of $10^{-4}$ mol/L.

INDUSTRIAL AVALABILITY

The novel 2-(α-hydroxypentyl)benzoates can be used for the preparation of pharmaceutical compositions, which is used for the prevention and treatment of the diseases such as cardiac ischemia, cerebral ischemia, arterial occlusion (obstruction) of heart and brain, etc.

What is claimed is:

1. A pharmaceutical composition for treating cardioischemia, cerebroischemia, cerebral arterial occlusion, and improving microcirculation of brain, comprising an effective amount of a compound of formula (I):

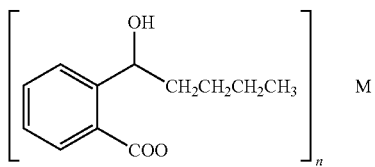

wherein M is a monovalent metal ion, a divalent metal ion, or an organic base group selected from anilinium group, benzyl ammonium group, morpholinium group and diethyl-ammonium group, and n is 1 or 2 and a pharmaceutically acceptable carrier.

2. The composition according to claim 1, wherein M is a potassium ion, a sodium ion, or a lithium ion.

3. The composition according to claim 1, wherein M is a calcium ion, a magnesium ion, or a zinc ion.

4. The pharmaceutical composition according to claim 1, which is in the form of a tablet, capsule, injection or lyophilized injection.

5. The composition according to claim 1, wherein M is a sodium or potassium ion.

* * * * *